US009326959B2

(12) United States Patent (10) Patent No.: US 9,326,959 B2
Wright et al. (45) Date of Patent: May 3, 2016

(54) OPIOID DOSAGE FORMS HAVING DOSE PROPORTIONAL STEADY STATE $C_{ave}$ AND AUC AND LESS THAN DOSE PROPORTIONAL SINGLE DOSE $C_{max}$

(75) Inventors: Curtis Wright, Rockport, MA (US); Robert Colucci, Newtown, CT (US); Ahmed El-Tahtawy, Brewster, NY (US)

(73) Assignee: Purdue Pharma, L.P., Stamford, CT (US)

( * ) Notice: Subject to any disclaimer, the term of this patent is extended or adjusted under 35 U.S.C. 154(b) by 1431 days.

(21) Appl. No.: 11/660,988

(22) PCT Filed: Aug. 30, 2005

(86) PCT No.: PCT/US2005/030892
§ 371 (c)(1),
(2), (4) Date: Sep. 27, 2007

(87) PCT Pub. No.: WO2006/028830
PCT Pub. Date: Mar. 16, 2006

(65) Prior Publication Data
US 2008/0132532 A1 Jun. 5, 2008

Related U.S. Application Data

(60) Provisional application No. 60/606,354, filed on Sep. 1, 2004.

(51) Int. Cl.
| A61K 9/22 | (2006.01) |
| A61K 9/20 | (2006.01) |
| A61K 38/00 | (2006.01) |
| A61K 31/44 | (2006.01) |
| A61K 31/194 | (2006.01) |
| A61K 9/16 | (2006.01) |
| A61K 31/485 | (2006.01) |
| A61F 13/00 | (2006.01) |
| A61F 6/06 | (2006.01) |
| A61F 9/02 | (2006.01) |
| A61K 9/48 | (2006.01) |
| A61K 9/52 | (2006.01) |

(52) U.S. Cl.
CPC ............ *A61K 31/194* (2013.01); *A61K 9/1629* (2013.01); *A61K 9/1635* (2013.01); *A61K 9/1658* (2013.01); *A61K 9/2077* (2013.01); *A61K 31/485* (2013.01)

(58) Field of Classification Search
None
See application file for complete search history.

(56) References Cited

U.S. PATENT DOCUMENTS

| 4,971,805 A | 11/1990 | Kitanishi et al. |
| 5,266,331 A | 11/1993 | Oshlack et al. |
| 5,273,760 A | 12/1993 | Oshlack et al. |
| 5,286,493 A | 2/1994 | Oshlack et al. |
| 5,324,351 A | 6/1994 | Oshlack et al. |
| 5,356,467 A | 10/1994 | Oshlack et al. |
| 5,472,712 A | 12/1995 | Oshlack et al. |
| 5,500,227 A | 3/1996 | Oshlack et al. |
| 5,508,042 A | 4/1996 | Oshlack et al. |
| 5,549,912 A | 8/1996 | Oshlack et al. |
| 5,580,578 A | 12/1996 | Oshlack et al. |
| 5,639,476 A | 6/1997 | Oshlack et al. |
| 5,656,295 A | 8/1997 | Oshlack et al. |
| 5,681,585 A | 10/1997 | Oshlack et al. |
| 5,958,459 A | 9/1999 | Chasin et al. |
| 5,965,161 A | 10/1999 | Oshlack et al. |
| 5,968,551 A | 10/1999 | Oshlack et al. |
| 6,024,982 A | 2/2000 | Oshlack et al. |
| 6,143,328 A | 11/2000 | Heafield et al. |
| 6,159,501 A * | 12/2000 | Skinhoj ................. 424/461 |
| 6,294,195 B1 | 9/2001 | Oshlack et al. |
| 6,335,033 B2 | 1/2002 | Oshlack et al. |
| 2002/0006438 A1* | 1/2002 | Oshlack et al. ............. 424/457 |
| 2002/0165248 A1 | 11/2002 | Wimmer et al. |
| 2003/0035837 A1 | 2/2003 | Sackler et al. |

FOREIGN PATENT DOCUMENTS

| EP | 1 449 350 A2 * | 6/2004 | ........... A61K 31/485 |
| EP | 1 449 530 | 8/2004 | |
| UA | 52679 C2 | 1/2003 | |
| UA | 55503 C2 | 4/2003 | |
| WO | WO 88/04922 | 7/1988 | |
| WO | WO 01/32148 | 5/2001 | |
| WO | WO 01/41762 | 6/2001 | |
| WO | WO 02/087512 | 11/2002 | |

OTHER PUBLICATIONS

Malonne et al., 2004, "Phamaracokinetic evaluation of a new oral sustained release dosage form of a tramadol." Brit. J. Clin. Pharm. 57(3): 270-278.

International Search Report and Written Opinion dated Mar. 27, 2006 issued for PCT/US2005/030892.

* cited by examiner

*Primary Examiner* — Jeffrey T Palenik

(74) *Attorney, Agent, or Firm* — Jones Day

(57) ABSTRACT

The present invention relates to, among other things, a kit comprising a plurality of dosage forms comprising a first dosage form and second dosage form each comprising a therapeutic agent, such as an opioid; wherein the dosage strength of the second dosage form is greater than that of the first dosage form; and wherein the steady state $C_{ave}$ and the steady state AUC of the first and second dosage forms are dose proportional and the single dose $C_{max}$ of the second dosage form is less than the minimum level for dose proportionality with respect to the first dosage form. The present invention also relates to methods of administering such plurality of dosage forms to a patient, comprising administering the first dosage form and thereafter administering the second dosage form.

24 Claims, 2 Drawing Sheets

US 9,326,959 B2

OPIOID DOSAGE FORMS HAVING DOSE PROPORTIONAL STEADY STATE $C_{ave}$ AND AUC AND LESS THAN DOSE PROPORTIONAL SINGLE DOSE $C_{max}$

CROSS-REFERENCE TO RELATED APPLICATIONS

This application is national stage entry of international application no. PCT/US05/30892, filed on Aug. 30, 2005 and published as WO 2006/028830 on Mar. 16, 2006, which claims priority from U.S. provisional application No. 60/606,354, filed on Sep. 1, 2004, the disclosure of each of which is incorporated herein in its entirety.

FIELD OF THE INVENTION

The present invention relates to a plurality of dosage forms comprising a first dosage form and a second dosage form comprising an opioid; wherein the second dosage form has a dosage strength or amount which is greater than that of the first dosage form; and wherein the steady state $C_{ave}$ and the steady state AUC of the first dosage form and the second dosage form are dose proportional; and the single dose $C_{max}$ of the second dosage form is less than the minimum level for dose proportionality with respect to the first dosage form. In one embodiment, the single dose of AUC the first dosage form and the second dosage form are also dose proportional. The present invention also relates to methods of administering such dosage forms to a patient, as well as to kits comprising such dosage forms and instructions for administration of the dosage forms to a patient.

BACKGROUND OF THE INVENTION

Opioids provide patients with meaningful beneficial effects, however, often patients also experience adverse effects from those same opioids. For example, opioids are useful as moderate to strong analgesic agents, but often cause other pharmacological side effects as well, such as drowsiness, respiratory depression, euphoria, nausea, dizziness, vomiting, pruritis and changes in mood. Such adverse effects can result in a patient's noncompliance, including discontinuation of therapy or missed doses.

There have been previous attempts in the art to increase the tamper resistance and patient acceptance of opioids. For example, controlled release dosage forms have been developed that release an active ingredient over many hours.

There remains a need in the art for improved dosage forms for administering opioids that can reduce adverse effects, and thus can potentially increase patient acceptance and abuse resistance.

All documents cited herein are incorporated by reference in their entireties for all purposes.

DEFINITIONS

Any reference herein to any opioid, any opioid antagonist or any therapeutic agent shall, unless otherwise stated, includes any pharmaceutically acceptable form of such pharmaceutical agent, such as the free form, any pharmaceutically acceptable salt form, any pharmaceutically acceptable base form, any pharmaceutically acceptable hydrate, any pharmaceutically acceptable solvate, any stereoisomer, any optical isomer, as well as any prodrug of such pharmaceutical agent and any pharmaceutically active analog of such pharmaceutical agent, and mixtures of any of the foregoing.

As used herein, the term "controlled release" refers to the in vivo release of an opioid from a dosage form in a controlled manner over an extended period of time. For example, a controlled release oral dosage form can release the opioid, e.g., over a 5 to 24 hour interval. As used herein, the terms "sustained release" and "controlled release" are synonymous.

As used herein, the term "dosage strength ratio" refers to the ratio of the dosage strength of one dosage form to the dosage strength of another dosage form.

As used herein, the terms "matrix multiparticulate(s)," and "matrix particles" refer to a plurality of units, preferably within a range of similar size and/or shape, and containing an opioid and one or more excipients, preferably including a hydrophobic controlled release material as described herein. Preferably, the matrix multiparticulates have a size in the range of from about 0.1 to about 12 mm in any dimension, more preferably from about 0.1 to about 5 mm. The matrix multiparticulates can be any geometrical shape. In certain embodiments, the matrix multiparticulates are made by a process comprising extrusion, and in one embodiment, the matrix multiparticulates are made by a process comprising melt extrusion.

As used herein, the terms "opioid" or "opioid agonist" refer to a therapeutic agent which binds, optionally stereo-specifically, to any one or more of several subspecies of opioid receptors and produces agonist activity.

As used herein, the phrase "opioid antagonist" refers to a therapeutic agent which binds, optionally stereo-specifically, to any one or more of several subspecies of opioid receptors and produces antagonist activity.

As used herein, the terms "patient" or "animal" include, but are not limited to, a cow, monkey, horse, sheep, pig, chicken, turkey, quail, cat, dog, mouse, rat, rabbit, and guinea pig, and is more preferably a mammal, and most preferably a human.

As used herein, the phrase "pharmaceutically acceptable salt," refers to a salt formed from an acid and the basic nitrogen group of an opioid. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from an opioid having an acidic functional group, such as a carboxylic acid or sulfonic acid functional group, and a pharmaceutically acceptable inorganic or organic base. Suitable bases include, but are not limited to, hydroxides of alkali metals such as sodium, potassium, cesium and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; N,N'-dibenzylethylenediamine, triethanolamine; inorganic acid salts such as hydrochloride, hydrobomide; organic acid salts such as formate, acetate, trifluoroacetate; and amino acids such as arginine, lysine, asparginate, glutamate and the like.

As used herein, the term "steady state" refers to a state in which the amount of the opioid reaching the system is approximately the same as the amount of the drug leaving the system. Thus, at steady state, the patient's body eliminates the opioid at approximately the same rate that the drug becomes available to the patient's system through absorption into the bloodstream. Generally, steady state is not achieved until after several sequential administrations of a dosage of an opioid at specified time intervals.

As used herein, the phrase "therapeutic agent" or "pharmaceutical agent" refers to a pharmaceutical agent that causes a biological effect when a sufficient amount is absorbed into the blood stream of a patient.

As used herein, the phrases "treatment of pain" or "treating pain" refer to the amelioration of pain or the cessation of pain or avoidance of the onset of pain in a patient.

As used herein, the term "wax-like substance" refers to any material that is normally solid at room temperature and has a melting point of from about 30 to about 100 degrees C.

SUMMARY OF THE INVENTION

The present invention relates to a plurality of dosage forms comprising a first dosage form having a first dosage strength or amount of an opioid, and a second dosage form having a second dosage strength of the opioid which is greater than the first dosage strength; wherein the first dosage form and the second dosage form each have a steady state $C_{ave}$, a steady state AUC and a single dose $C_{max}$; and wherein the steady state $C_{ave}$ and the steady state AUC of the first dosage form and the second dosage form are dose proportional and the single dose $C_{max}$ of the second dosage form is less than the minimum level for dose proportionality with respect to the first dosage form. In certain embodiments, the single dose $C_{max}$ of the second dosage form is 75% or less of the $C_{max}$ of the first dosage form times the dosage strength ratio of the second dosage form to the first dosage form. The invention also relates to a method of administering such dosage forms comprising administering the first dosage form and, thereafter, administering the second dosage form.

In one embodiment, the first dosage form and the second dosage form each have a single dose AUC and the single dose AUC of the first dosage form and the second dosage form are also dose proportional. In one embodiment, the dosage forms are each controlled release dosage forms. In certain embodiments, the opioid is hydrocodone.

The present invention also relates to a plurality of dosage forms comprising a first dosage form comprising a first dosage strength of an opioid; a second dosage form comprising a second dosage strength of the opioid; and a third dosage form comprising a third dosage strength of the opioid; wherein the third dosage strength is greater than the second dosage strength and the second dosage strength is greater than the first dosage strength; and wherein the first dosage form, the second dosage form and the third dosage form each have a steady state Cave, a steady state AUC and a single dose $C_{max}$; and the steady state $C_{ave}$ and the steady state AUC of the first dosage form, the second dosage form and the third dosage form are each dose proportional with respect to each other; the single dose $C_{max}$ of the second dosage form is less than the minimum level for dose proportionality with respect to the first dosage form; and the single dose $C_{max}$ of the third dosage form is less than the minimum level for dose proportionality with respect to the second dosage form. In certain embodiments, the single dose $C_{max}$ of the second dosage form is 75% or less of the single dose $C_{max}$ of the first dosage form times the dosage strength ratio of the second dosage form to the first dosage form; and the single dose Cmax of the third dosage form is 75% or less of the single dose $C_{max}$ of the second dosage form times the dosage strength ratio of the third dosage form to the second dosage form. The invention also relates to a method of administering such dosage forms comprising administering the first dosage form, thereafter administering the second dosage form, and thereafter, administering the third dosage form.

In one embodiment, the first dosage form, the second dosage form and the third dosage form are each controlled release dosage forms. In one embodiment, the single dose AUC of the first dosage form, the second dosage form and the third dosage form are each dose proportional. In certain embodiments, the opioid is hydrocodone.

The present invention also relates to a kit for treating a patient comprising a plurality of dosage forms according to the invention, and a set of printed instructions directing the administration of the first dosage form to the patient, and thereafter, the administration of the second dosage form to the patient, and if present, thereafter, the administration of the third dosage form to the patient.

The present invention can be understood more fully by reference to the following figures, detailed description and examples, which are intended to exemplify non-limiting embodiments of the invention.

DETAILED DESCRIPTION OF THE INVENTION

Figure 1:
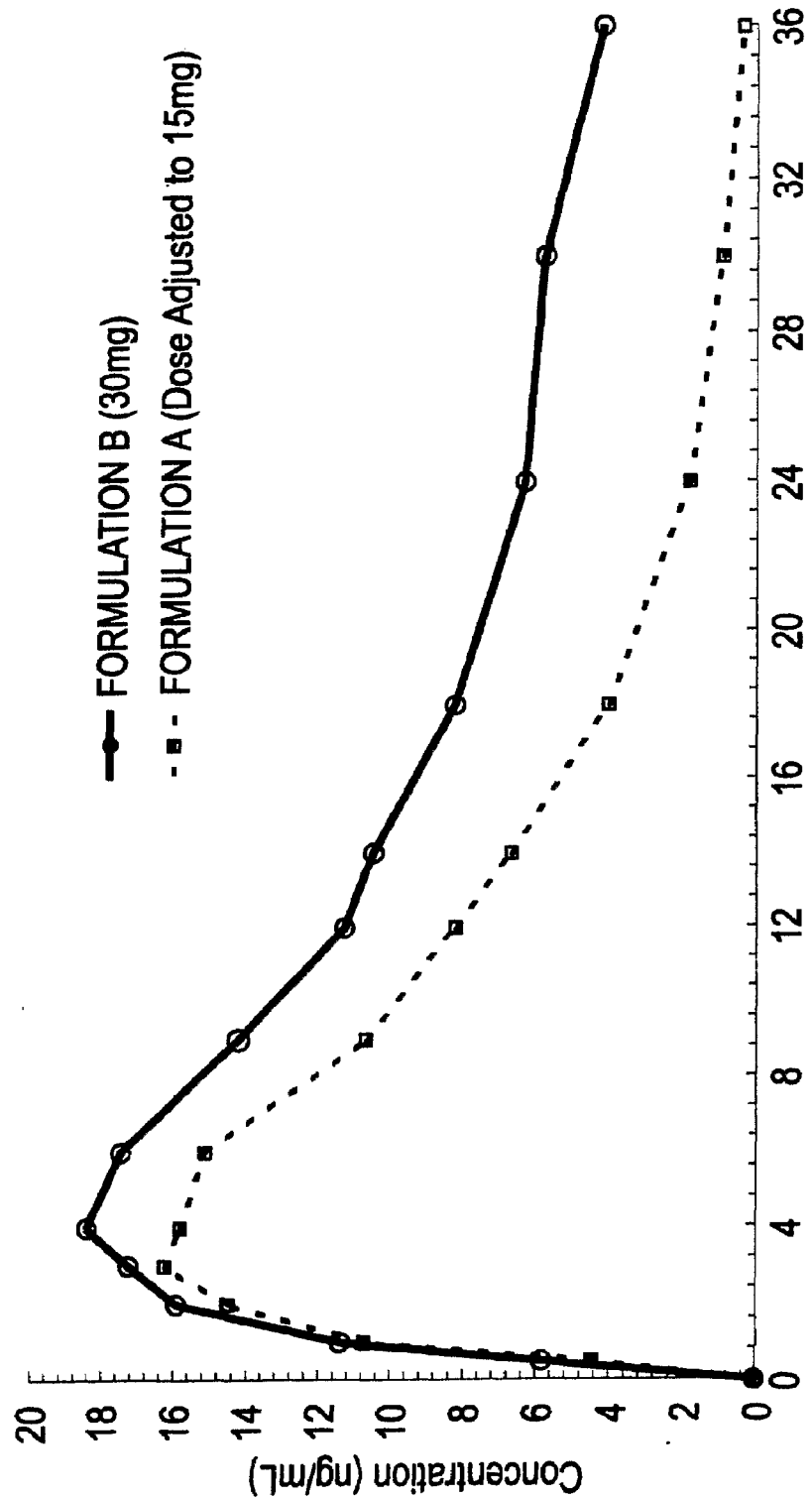
FIG. 1 shows opioid plasma concentration-time profiles for a single dose of the 30 mg hydrocodone dosage form of Formulation A of Example 1 and for a single dose of the hydrocodone dosage form of Formulation B of Example 1, dose adjusted to 15 mg, respectively.

It is the belief of the inventors that delivery release characteristics (rate, extent, profile) can influence a patient's acceptance of medications and the tamper resistance of medications. For example, certain medications having a faster drug delivery rate (as seen with certain immediate release medications) are reported to have lower patient acceptance and increased adverse effects. The inventors believe that immediate release dosage forms of certain therapeutic agents can also present decreased abuse resistance and greater reinforcing properties compared to medications that have a slower drug delivery rate. Additionally, the inventors believe that drug abusers often tend to prefer higher dosage strength dosage forms in order to experience the euphoric effects of the drug.

The present invention provides a plurality of dosage forms comprising a first dosage form having a first dosage strength of an opioid, such as hydrocodone; and a second dosage form having a second dosage strength of the opioid; wherein the second dosage strength is greater than the first dosage strength; and wherein the first dosage form and the second dosage form each have a steady state $C_{ave}$, a steady state AUC and a single dose $C_{max}$, and the steady state $C_{ave}$ and the steady state AUC of the first dosage form and the second dosage form are dose proportional, and the single dose $C_{max}$ of the second dosage form is less than the minimum level for dose proportionality with respect to the first dosage form.

In certain embodiments, the single dose $C_{max}$ of the second dosage form is 75% or less, e.g., 70% or less, 65% or less or 60% or less, of the $C_{max}$ of the first dosage form times the dosage strength ratio of the second dosage form to the first dosage form.

In one embodiment, the first dosage form and the second dosage form each have a single dose AUC, and the single dose AUC of the second dosage form and the first dosage form are also dose proportional.

In certain embodiments, the present invention provides a plurality of dosage forms comprising three dosage forms, a first dosage form, a second dosage form, and a third dosage form, each comprising of an opioid, such as hydrocodone. In these embodiments, the dosage strength of the third dosage form is greater than the dosage strength of the second dosage form, and the dosage strength of the second dosage form is greater than that of the first dosage form. The steady state $C_{ave}$ and the steady state AUC of the first, second and third dosage forms are dose proportional; the single dose $C_{max}$ of the second dosage form is less than the minimum level for dose proportionality with respect to the first dosage form, and the single dose $C_{max}$ of the third dosage form is less than the minimum level for dose proportionality with respect to the second dosage form. In certain embodiments, the single dose $C_{max}$ of the third dosage form is 75% or less, e.g., 70% or less, 65% or less or 60% or less, of the $C_{max}$ of the first dosage form times the dosage strength ratio of the second dosage form to the first dosage form. Similarly, in certain embodiments, the $C_{max}$ of the third dosage form is 75% or less, e.g., 70% or less, 65% or less or 60% or less, of the $C_{max}$ of the second dosage form times the dosage strength ratio of the third dosage form to the second dosage form.

In one embodiment, the single dose AUC of the first, second and third dosage forms, respectively, are also dose proportional.

It is anticipated that drug abusers will find the higher dosage strength dosage form(s) made in accordance with the invention to be less desirable to abuse due to the above-described levels of $C_{max}$ which are less than dose proportional to the lower dosage strength dosage form(s). Additionally, it is anticipated that patients who have a need to increase the dosage strength of medication will experience less adverse effects, and thus find the higher dosage strength dosage form(s) of the present invention to be more acceptable and tolerable.

In addition to comprising the opioid having the characteristics described in the claims, the dosage forms of the present invention can contain additional compounds, including but not limited to, one or more additional therapeutic agents and/or opioid antagonists and/or aversive agents.

Examples of such therapeutic agents include, but are not limited to, antihistamines (e.g., dimenhydrinate, diphenhydramine, chlorpheniramine and dexchlorpheniramine maleate), analgesics (e.g., aspirin, acetominophen, opioids, etc.), non-steroidal anti-inflammatory agents (e.g., naproxyn, diclofenac, indomethacin, ibuprofen, sulindac), anti-emetics (e.g., metoclopramide), anti-epileptics (e.g., phenytoin, meprobamate and nitrezepam), vasodilators (e.g., nifedipine, papaverine, diltiazem and nicardirine), anti-tussive agents and expectorants (e.g., codeine phosphate), anti-asthmatics (e.g., theophylline), antacids, anti-spasmodics (e.g., atropine, scopolamine), antidiabetics (e.g., insulin), diuretics (e.g., ethacrynic acid, bendrofluazide), anti-hypotensives (e.g., propranolol, clonidine), antihypertensives (e.g., clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics; antidiarrheals, mucolytics, sedatives, decongestants, laxatives, vitamins, stimulants (including appetite suppressants such as phenylpropanolamine), as well as salts, hydrates, solvates and other pharmaceutically acceptable forms of the same.

Examples of opioid antagonists include but are not limited to, naloxone, naltrexone, nalmefene, nalbuphine, nalorphine, cyclazacine, cyclazocine, levallorphan, pharmaceutically acceptable salts thereof, and mixtures of any two or more of the foregoing. Examples of aversive agents include, but are not limited to a bittering agent, an irritant and a gelling agent. Additional examples and details of aversive agents are set forth in U.S. Patent Application Publication No. 2003/0124185 A1 to Oshlack et al., which is expressly incorporated herein in its entirety for all purposes. The dosage form can be formulated in such a manner that the opioid antagonist and/or the aversive agent are only released upon tampering with the dosage form.

The dosage forms used in the methods of the present invention can be prepared in accordance with any technology known in the art, including but not limited to that exemplified below.

OPIOIDS

Any opioid may be incorporated in the dosage forms of the present invention, including but not limited to, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, diamorphone, dihydrocodeine, dihydromorphine, dihydromorphone, dihydroisomorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, heroin, hydrocodone, hydromorphone, hydromorphodone, hydroxypethidine, isomethadone, ketobemidone, levallorphan, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papaveretum, paregoric, pentazocine, phenadoxone, phendimetrazine, phendimetrazone, phenomorphan, phenazocine, phenoperidine, piminodine, piritramide, propheptazine, promedol, properidine, propiram, propoxyphene, propylhexedrine, sufentanil, tilidine, tramadol, pharmaceutically acceptable salts thereof and mixtures of any two or more of the foregoing.

In certain embodiments, the opioid is hydrocodone, morphine, hydromorphone, oxycodone, codeine, levorphanol, meperidine, methadone, oxymorphone, buprenorphine, fentanyl, dipipanone, heroin, tramadol, etorphine, dihydroetorphine, dihydrocodeine, dihydromorphine, butorphanol, levorphanol, and mixtures of any two or more of the foregoing. In certain embodiments, the opioid is selected from the group consisting of oxycodone, hydrocodone, fentanyl, buprenorphine, and mixtures of any two or more of the foregoing. In one embodiment, the opioid is hydrocodone.

The analgesically effective amount of opioid present in the dosage form will depend in part on the specific opioid and the dosage form characteristics and formulation. It is well within the purview of one skilled in the art to readily determine the analgesically effective amount of an opioid needed for a particular indication.

DOSAGE FORMS

The present invention includes dosage forms which can vary in release rate from immediate release to controlled release. The dosage forms of the invention include oral dosage forms, including but not limited to tablets, caplets, gelcaps and capsules, as well as anal suppositories and vaginal suppositories.

In one embodiment, the present invention includes controlled release dosage forms such as controlled release matrix formulations comprising an opioid and a controlled release material. The sustained release material can be hydrophobic or hydrophilic as desired. The controlled release dosage forms can be made and formulated according to any method known in the art.

In certain embodiments, controlled release dosage form of the present invention can be prepared as granules, spheroids, matrix multiparticulates, etc., which comprise the opioid in a controlled release matrix, which can be encapsulated or compressed into a tablet.

Techniques and compositions for making tablets (compressed and molded), capsules (hard and soft gelatin) and pills are also described in Remington's Pharmaceutical Sciences, 18$^{th}$ ed. Arthur Osol, 1553-93 (1990), which is incorporated herein in its entirety for all purposes. In one embodiment, a suitable amount of multiparticulates are compressed into an oral tablet using conventional tableting equipment and standard techniques. In yet another embodiment, the extrudate can be shaped into tablets as described in U.S. Pat. No. 4,957,681 to Klimesch et al., which is incorporated herein in its entirety for all purposes.

In certain embodiments, the opioid can be dispersed in a controlled release matrix. Any controlled release matrix can be used in the oral dosage form of the invention. Controlled release matrices for dosage forms are well known in the art (See, e.g., Remingtons Pharmaceutical Sciences, 18th ed. Mack Publishing Co., Easton, Pa., 1990, p. 1684-1685), which is incorporated herein in its entirety for all purposes. Additional examples of useful controlled release matrices are described in U.S. Pat. Nos. 5,958,459; 5,965,161; 5,968,551; 6,294,195 and U.S. Pat. No. 6,335,033, each to Oshlack et al. and U.S. Pat. No. 6,143,328 to Heafield et al., each of which is incorporated herein in its entirety for all purposes.

The controlled release matrix can comprise a fusible hydrophobic material, optionally combined with a hydrophilic material. The hydrophobic fusible material can be, for example, a hydrophobic polymer or a natural or synthetic wax or oil, such as hydrogenated vegetable oil or hydrogenated castor oil, preferably having a melting point of from about 35 to 100° C., more preferably from about 45 to 90° C. The hydrophilic material can be a hydrophilic polymer; a water soluble fusible material, such as polyethylene glycol; or a water soluble particulate material, such as dicalcium phosphate or lactose. However, any pharmaceutically acceptable hydrophobic or hydrophilic material capable of imparting controlled release of the opioid can be used in accordance with the present invention.

The therapeutic agent dispersed in a controlled release matrix can be prepared by formulating the therapeutic agent with a non-fusible material. component other than the fusible component. Suitable non-fusible materials for inclusion in a controlled release matrix include, but are not limited to:

(a) hydrophilic or hydrophobic polymers, such as gums, cellulose ethers, protein-derived materials, nylon, acrylic resins, polylactic acid, polyvinylchloride, starches, polyvinylpyrrolidones, and cellulose acetate phthalate. For example, cellulose ethers, preferably substituted cellulose ethers such as alkylcelluloses (e.g., ethylcellulose), C1-C6 hydroxyalkylcelluloses (e.g., hydroxypropylcellulose, hydroxypropylmethylcellulose and hydroxyethyl cellulose), carboxyalkylcelluloses and acrylic resins (e.g., acrylic acid polymers and copolymers; and methacrylates such as methacrylic acid polymers and copolymers) are useful. The controlled release matrix can conveniently contain between 1% and 80% (by weight) of the hydrophobic and/or hydrophilic polymer.

(b) digestible, long chain (C8-C50, preferably C8-C40) substituted or unsubstituted hydrocarbons, such as hydrogenated vegetable oils; fatty alcohols, such as lauryl, myristyl, stearyl, cetyl or, preferably cetostearyl alcohol; fatty acids, including fatty acid glycerides (mono-, di- and tri-glycerides), hydrogenated fats, glyceryl esters of fatty acids, for example, glyceryl monostearate; vegetable oils; mineral oils; normal waxes; stearic acid and natural and synthetic waxes, such as beeswax, glycowax, castor wax, and carnauba wax, and other wax-like substances; and hydrophobic and hydrophilic materials having hydrocarbon backbones. Hydrocarbons having a melting point of between about 25° C. and 90° C. are useful. For example, fatty (aliphatic) alcohols are useful in certain embodiments. The controlled release matrix can contain up to 80% (by weight) of at least one digestible, long chain hydrocarbon.

(c) Polyalkylene glycols. The controlled release matrix can contain up to 60% (by weight) of at least one polyalkylene glycol.

A suitable controlled release matrix for use in the oral dosage form of the invention can comprise one or more cellulose ethers or acrylic resins, one or more C12-C36, e.g., C12-C22, aliphatic alcohols, and/or one or more hydrogenated vegetable oils. One particular suitable matrix comprises one or more alkylcelluloses, one or more C12-C22 aliphatic alcohols and one or more polyalkylene glycols. For example, the matrix can contain between about 0.5% and 60%, e.g., between 1% and 50% (by weight) of the cellulose ether.

The acrylic resin can be a methacrylate such as methacrylic acid copolymer USNF Type A (EUDRAGIT L), Type B (EUDRAGIT S), Type C (EUDRAGIT L 100-55), EUDRAGIT NE 30 D, EUDRAGIT E, EUDRAGIT RL, or EUDRAGIT RS (commercially available from Rohm Pharma GmbH, Weiterstat, Germany). For example, the matrix can contain between about 0.5% and 60% by weight, e.g., between 1% and 50% by weight, of the acrylic resin.

In certain embodiments, the dosage form comprises a controlled release matrix comprising the opioid and at least one water soluble hydroxyalkyl cellulose, at least one C12-C36, preferably C14-C22, aliphatic alcohol, and, optionally, at least one polyalkylene glycol. The hydroxyalkyl cellulose can be a hydroxy (C1 to C6) alkyl cellulose, such as hydroxypropylcellulose, hydroxypropylmethylcellulose, and most preferably, hydroxyethyl cellulose. The amount of the at least one hydroxyalkyl cellulose in the present dosage form can be determined by, inter alia, the precise rate of release of the opioid required. The aliphatic alcohol can be, for example, lauryl alcohol, myristyl alcohol, stearyl alcohol, cetyl alcohol or cetostearyl alcohol and mixtures of any two or more of the foregoing. The amount of the aliphatic alcohol to be included in the present dosage form can be determined, as above, by, inter alia, the precise rate of release of the opioid required. It can also depend on whether at least one polyalkylene glycol is present in, or absent from, the dosage form.

In one embodiment, in the absence of polyalkylene glycol, the matrix can contain between about 1% and 50%, e.g., between about 2% and 36% by weight of the aliphatic alcohol. In another embodiment, polyalkylene glycol is present in the oral dosage form, and the combined weight of the aliphatic alcohol and the polyalkylene glycol can constitute between about 2% and 40%, e.g., between about 2 and 36% by weight of the total dosage form.

In certain embodiments, the polyalkylene glycol can be, for example, polypropylene glycol or, preferably, polyethylene glycol. For example, the number average molecular weight of the at least one polyalkylene glycol can be between 200 and 15,000, e.g., between 400 and 12,000 or between 1,500 and 12,000.

In certain embodiments, the controlled release of the opioid can be affected by various inducers, for example pH, temperature, enzymes, water, or other physiological conditions or compounds.

The controlled release matrix containing the opioid can readily be prepared, for example, by dispersing the opioid in the components of the matrix using conventional pharmaceutical techniques including, but not limited to, melt-granulation, wet granulation, dry blending, dry granulation, co-precipitation, extrusion and melt extrusion.

Incorporation of the opioid in the matrix can be effected, for example, by the following steps:

(a) directly metering into an extruder a hydrophobic sustained release material, the opioid, and an optional binder material;

(b) heating the homogeneous mixture; extruding the homogeneous mixture to thereby form strands; cooling the strands containing the homogeneous mixture (if necessary);

(c) cutting the strands into matrix multiparticulates having a size ranging from about 0.1 mm to about 5 mm in any dimension; and (d) dividing the particles into unit doses. In this aspect of the invention, a relatively continuous manufacturing procedure is realized.

Typical melt-extrusion production systems suitable for use in accordance with the present invention include a suitable extruder drive motor having a variable speed and constant torque control, start-stop controls, and ammeter. In addition, the production system typically includes a temperature control console that includes temperature sensors, cooling means and temperature indicators throughout the length of the extruder. Further, the production system typically includes an extruder, such as a twin-screw extruder, which comprises two counter-rotating intermeshing screws enclosed within a cylinder or barrel having an aperture or die at the exit thereof. The feed materials enter through a feed hopper; are moved through the barrel by the screws; and are forced through the die into strands, which are thereafter conveyed, such as by a continuous movable belt, to allow for cooling and being directed to a pelletizer or other suitable device to render the extruded strands into the matrix multiparticulate system. For example, the pelletizer can comprise rollers, a fixed knife, a rotating cutter and the like. Suitable instruments and systems are available from distributors such as C. W. Brabender Instruments, Inc. of South Hackensack, N.J. Other suitable apparatus will be apparent to those of ordinary skill in the art. For example, the dosage forms can be prepared using a Werner-Pfleiderer twin screw extruder.

The diameter of the extruder aperture or exit port can be adjusted to vary the thickness of the extended strands. Furthermore, the exit port of the extruder need not be round; it can be, e.g., oblong, rectangular, etc. The exiting strands can be reduced to particles using, e.g., a hot wire cutter, guillotine, etc.

A matrix multiparticulate system can be, for example, in the form of granules, spheroids or pellets, depending upon the extruder exit port. In one embodiment, dosage forms are prepared that include an effective amount of matrix multiparticulates within a capsule. For example, a plurality of the matrix multiparticulates can be placed in a gelatin capsule in an amount sufficient to provide an effective controlled release dose when ingested and contacted by gastrointestinal fluid.

The dosage forms of the present invention can comprise combinations of matrix multiparticulates containing opioid and having differing formulations and/or characteristics. Furthermore, the controlled release dosage forms can also include a portion of the total amount of opioid in immediate release form to provide a prompt therapeutic effect. The immediate release opioid can be incorporated, e.g., as separate multiparticulates within a gelatin capsule, or can be coated on the surface of, e.g., matrix multiparticulates.

Additional examples of methods of making controlled release dosage forms that can be used in accordance with the present invention include those described in U.S. Pat. Nos. 5,266,331; 5,324,351; 5,356,467; 5,472,712; 5,500,227; 5,508,042; 5,549,912; 5,656,295; and U.S. Pat. No. 6,024,982, each to Oshlack et al., and U.S. Pat. No. 5,958,459 to Chasin et al., the contents of which are each expressly incorporated herein for all purposes.

In certain embodiments, the dosage forms or the uncoated or coated sustained release spheroids, granules, or matrix multiparticulates containing the opioid can be cured until an endpoint is reached at which the sustained release spheroids, granules, or matrix multiparticulates provide a stable dissolution. The curing endpoint can be determined by comparing the dissolution profile (curve) of the dosage form immediately after curing to the dissolution profile (curve) of the dosage form after exposure to accelerated storage conditions of, e.g., at least one month at a temperature of 40 degrees C. and a relative humidity of 75%. Cured formulations are described in detail in U.S. Pat. Nos. 5,273,760; 5,286,493; 5,580,578; 5,639,476 and U.S. Pat. No. 5,681,585, each to Oshlack et al., the disclosures of which are each incorporated herein in their entirety for all purposes.

In addition to the above ingredients, the dosage forms can also contain suitable quantities of other materials, e.g., plasticizers, diluents, lubricants, binders, granulating aids, colorants, flavorants and glidants that are conventional in the pharmaceutical art. In certain embodiments, these additional materials can be present in amounts up to about 50% by weight of the formulation, if desired. The quantities of these additional materials sufficient to provide the desired effect to the desired formulation can be determined by one of ordinary skill. For example, the addition of a small amount of talc to the sustained release coating reduces the tendency of the aqueous dispersion to stick during processing, and acts as a polishing agent. Specific examples of pharmaceutically acceptable carriers and excipients that can be used to formulate oral dosage forms are described in the Handbook of Pharmaceutical Excipients, American Pharmaceutical Association (1986).

The following examples illustrate various aspects of the present invention. They are not to be construed to limit the claims in any manner whatsoever. Rather, pluralities of dosage forms which have characteristics which are either more similar to one another or less similar to one another may also fall within the scope of the present invention.

EXAMPLE

Example 1

Hydrocodone Bitartrate

A study was conducted which served to compare two oral controlled release opioid formulations having different release characteristics. In that study, healthy male volunteers were randomized into a single-dose, 4-way crossover pharmacokinetic study with hydrocodone bitartrate controlled release oral tablets. The initial objective of the study was to assess the pharmakokinetic ("PK") profiles and then in vitro/in vivo correlation ("IV/IVC") for 30 mg dosage strength controlled release hydrocodone formulations having differing dissolution profiles. The hydrocodone bitartrate controlled release ("HYCR") oral dosage forms included the following: 1) Formulation A, a 30 mg tablet having a first in vitro dissolution profile; and 2) Formulation B, a 30 mg tablet having an in vitro dissolution profile which was slower than that of Formulation A for the time period from 1 to 12 hours.

Formulation Compositions

Two formulations having varied in vitro dissolution profiles which were used in this study are as follows:

FORMULATION A

| Ingredient | Amt/Unit (mg) | Amt/batch (gram) | Weight Fraction |
|---|---|---|---|
| Hydrocodone Bitartrate | 30.0 | 150.0 | |
| Spray Dried Lactose | 119.2 | 596.0 | |
| Povidone | 8.0 | 40.0 | |
| Eudragit RS30D (Solids) | 14.0 | 70.0 | |
| Triacetin | 2.8 | 14.0 | |
| Stearyl Alcohol | 40.0 | 200.0 | |
| Talc | 4.0 | 20.0 | |
| Magnesium Stearate | 2.0 | 10.0 | |
| Opadry Red YS1-15597-A | 10.0 | 50.0 | |
| Purified Water | * | * | * |
| Total | 230 | 1150.0 | 1.00 |

*Used for processing and remains in product as residual moisture only.

FORMULATION B

| Ingredient | Amt/Unit (mg) | Amt/batch (gram) | Weight Fraction |
|---|---|---|---|
| Hydrocodone Bitartrate | 30.0 | 150.0 | .13 |
| Spray Dried Lactose | 90.0 | 450.0 | .39 |
| Povidone | 8.0 | 40.0 | .03 |
| Eudragit RS30D (Solids) | 30.0 | 150.0 | .13 |
| Triacetin | 6.0 | 30.0 | .03 |
| Stearyl Alcohol | 50.0 | 250.0 | .22 |
| Talc | 4.0 | 20.0 | .02 |
| Magnesium Stearate | 2.0 | 10.0 | .01 |
| Opadry Red YS1-15597-A | 10.0 | 50.0 | .04 |
| Purified Water | * | * | * |
| Total | 230.0 | 1150.0 | 1 |

*Used for processing and remains in product as residual moisture only.

To prepare tablets having these hydrocodone bitartrate formulations, the specified amount of hydrocodone bitartrate was measured out into 15 mg or 30 mg dosages, depending upon the formulation. The selected dosage amount of hydrocodone was then sprayed with a eudragit/triacetin dispersion. Dried lactose and povidone were then sprayed on the composition using a fluid bed granulator. After spraying, the granulation was discharged and passed through a mill. Melted stearyl alcohol was then added to the granulation using a mixer, and the granulation was allowed to cool. The cooled granulation was passed through a mill. Talc and magnesium stearate were added in a mixer in order to lubricate the granulation. The granulation was then compressed into tablets using a tablet press. After forming the tablet, an aqueous film coat was applied to the tablets.

Dissolution Method:

The in vitro dissolution for the two formulations was obtained using U.S.P. Apparatus II (Paddle Method) with 700 ml of simulated gastric fluid for the first 55 minutes at 100 rpm and 37° C. followed by 900 ml of simulated intestinal fluid for the remainder of testing. The results were measured by high performance liquid chromatography. The results are set forth in Table 1 below:

TABLE 1

| | Dissolution (%) | |
|---|---|---|
| Hour | A | B |
| 0 | 0% | 0% |
| 1 | 49.0% | 25.5% |
| 2 | 60.1% | 31.7% |
| 4 | 76.1% | 41.5% |
| 8 | 93.0% | 54.7% |
| 12 | 97.3% | 65% |

Clinical Study Protocol:

The adverse effects of hydrocodone bitrate were studied on 32 healthy, young adult male volunteers in a single dose, 4-way, randomized, crossover study. Thirty subjects completed the study, and two subjects were discontinued due to protocol violations. Each patient was administered either one 30 mg dosage form of Formulation A or one 30 mg dosage form of Formulation B or one 30 mg dosage form or 30 mg of one of two other controlled release hydrocodone formulations which had dissolution profiles slower than Formulation A and faster than Formulation B over a 12 hour period. The subjects were screened for a period up to 14 days. The study was a single dose, 4-way, randomized crossover study. All treatments were administered under fasted conditions having dose periods separated by a 7-day washout. The subjects were screened for entry into the study and randomly assigned to a treatment sequence for crossover dosing.

Table 2 below presents common adverse events (irrespective of relationship to study drug), i.e., those with an incidence of ≥5%, for any treatment by COSTART (Coding System for Thesaurus of Adverse Reaction Terms) term.

TABLE 2

| | Common Adverse Events | |
|---|---|---|
| | Number (%) of Subjects | |
| Body System Adverse Event | Formulation A (N = 30) | Formulation B (N = 31) |
| Total Number (%) of Subjects with Adverse Events | 13 (43.3) | 4 (12.9) |
| | Digestive | |
| Nausea | 6 (20) | — |
| Vomiting | 3 (10) | 1 (3.2) |
| | Nervous | |
| Dizziness | 9 (30) | 1 (3.2) |
| Somnolence | 2 (6.7) | — |
| | Skin | |
| Pruritus | 2 (6.7) | — |

A lower incidence of adverse events was reported with Formulation B (n=4) than with Formulation A (n=8). The common (incidence ≥5%) adverse events (vomiting, dizziness, nausea, pruritus, and somnolence) are among those expected from hydrocodone treatment. Significantly, the number of adverse events, including those considered to be related to treatment, the number of subjects reporting adverse events, and the number of moderate adverse events (none was rated severe) were all lower with Formulation B than with Formulation A. These results indicate that the different release characteristics of Formulation B compared to Formulation A resulted in a decrease in adverse effects which was greater than expected.

Based in part on the foregoing study results, the inventors believe that beneficial results would be obtained by formulating a plurality of dosage forms wherein the second dosage form has a dosage strength greater than the first dosage form, and wherein the steady state Cave and the steady state AUC of the first and second dosage forms are dose proportional and the single dose $C_{max}$ of the second dosage form is less than the minimum level for does proportionality with respect to the first dosage form. The inventors also believe that it would further be beneficial for this first and second dosage forms to have dose proportional single dose AUC values.

The inventors dose adjusted the Formulation A dosage form from 30 mg to 15 mg. The pharmacokinetic data for Formulation A dose adjusted to 15 mg and Formulation B (30 mg) are set forth in Tables 3 and 4 below:

TABLE 3

Single Dose

| Formula | Cmax (ng/mL) | AUCt (hr * ng/mL) | AUCINF (hr * ng/mL) |
|---|---|---|---|
| Formulation A (dose adjusted to 15 mg) | 16.24 | 212.44 | 214.85 |
| Formulation B (30 mg) | 18.40 | 344.45 | 462.71 |

TABLE 4

Steady State

| Formula | Cmax, ss (ng/mL) | AUCt, ss (hr * ng/mL) | Cmin, ss (ng/mL) | Cavg (ng/mL) |
|---|---|---|---|---|
| Formulation A (dose adjusted to 15 mg) | 23.91 | 215.64 | 10.46 | 17.97 |
| Formulation B (30 mg) | 41.60 | 431.94 | 27.23 | 36.00 |

Figure 2:
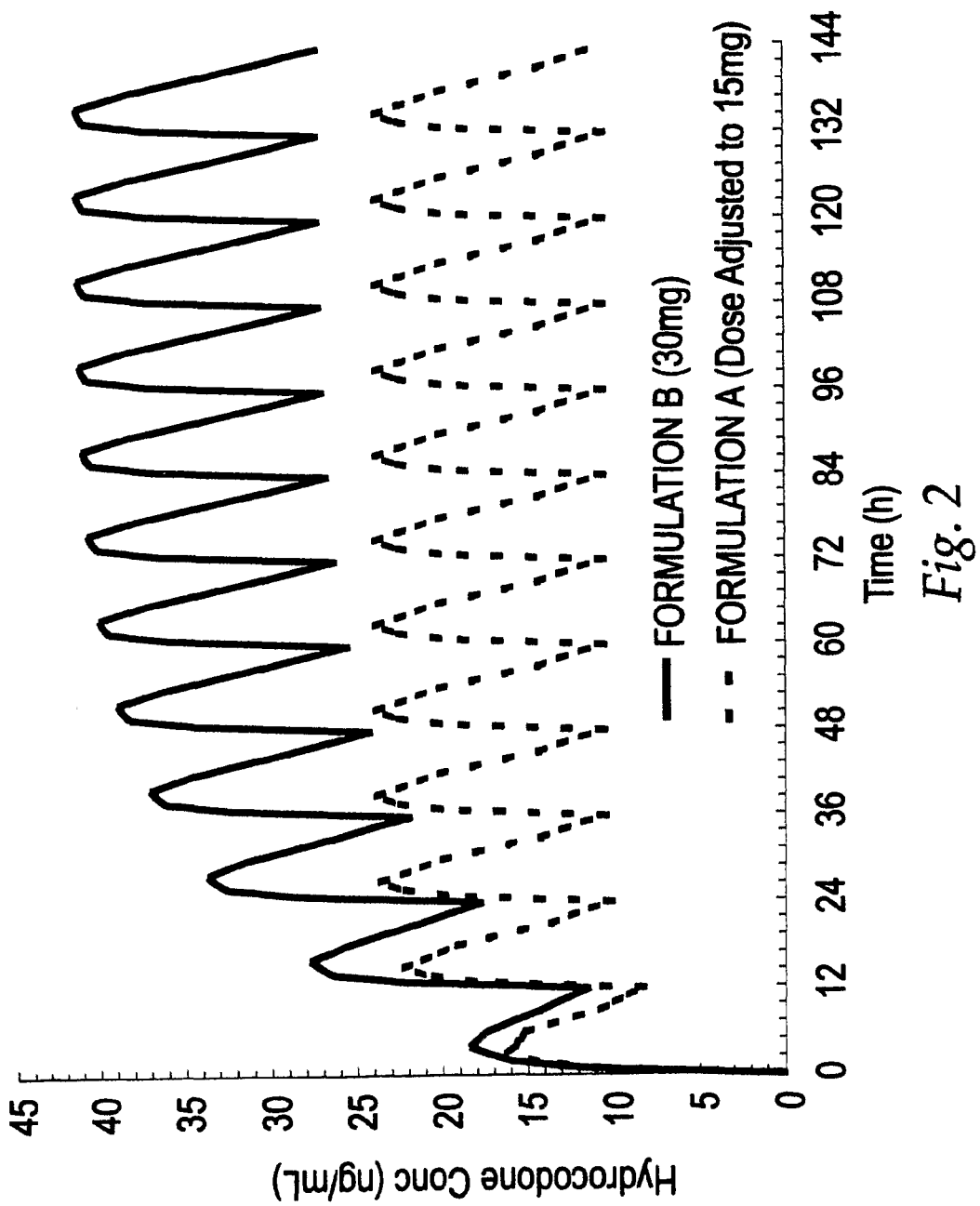
FIG. 2 shows opioid plasma concentration-time profiles for multiple doses of the dosage forms of FIG. 1, based on super positioning.

A plot setting forth the blood plasma concentration (ng/ml) versus time (h) for a single dose of Formulation A (dose adjusted to 15 mg) and Formulation B (30 mg) is shown in FIG. 1. A plot setting forth the blood plasma concentration (ng/ml) versus time (h) for multiple doses, i.e., steady state, of Formulation A (dose adjusted to 15 mg) and Formulation B (30 mg), based on super positioning, is shown in FIG. 2.

What is claimed is:

1. A kit comprising: a) a first dosage form comprising a first dosage strength of an opioid; and b) a second dosage form comprising a second dosage strength of the opioid; wherein the second dosage strength is greater than the first dosage strength; and wherein the first dosage form and the second dosage form each have a steady state $C_{ave}$, a steady state AUC and a single dose $C_{max}$; wherein the steady state $C_{ave}$ and the steady state AUC of the first dosage form and the second dosage form are dose proportional and the single dose $C_{max}$ of the second dosage form is less than the minimum level for dose proportionality with respect to the first dosage form; wherein the first dosage form and the second dosage form are each sustained release dosage forms; wherein the first dosage form and the second dosage form are each a tablet, a capsule, a caplet or a gelcap; and wherein the first dosage form and the second dosage form do not comprise a portion of the opioid in immediate release form.

2. The kit of claim 1, wherein the first dosage form and the second dosage form each have a single dose AUC and the single dose AUC of the first dosage form and the second dosage form are dose proportional.

3. The kit of claim 2, wherein the first dosage form and the second dosage form are each oral dosage forms.

4. The kit of claim 1, wherein the first dosage form and the second dosage form are each oral dosage forms.

5. The kit of claim 1, wherein the opioid is selected form the group consisting of alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, diamorphone, dihydrocodeine, dihydromorphine, dihydromorphone, dihydroisomorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, heroin, hydrocodone, hydromorphone, hydromorphodone, hydroxypethidine, isomethadone, ketobemidone, levallorphan, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papaveretum, paregoric, pentazocine, phenadoxone, phendimetrazine, phendimetrazone, phenomorphan, phenazocine, phenoperidine, piminodine, piritramide, propheptazine, promedol, properidine, propiram, propoxyphene, propylhexedrine, sufentanil, tilidine, tramadol, and mixtures of any two or more of the foregoing.

6. The kit of claim 5, wherein the opioid is selected form the group consisting of hydrocodone, morphine, hydromorphone, oxycodone, codeine, levorphanol, meperidine, methadone, oxymorphone, buprenorphine, fentanyl, dipipanone, heroin, tramadol, etorphine, dihydroetorphine, dihydrocodeine, dihydromorphine, butorphanol, levorphanol, and mixtures of any two or more of the foregoing.

7. The kit of claim 5, wherein the opioid is hydrocodone.

8. The kit of claim 1, further comprising a third dosage form comprising a third dosage strength of the opioid; wherein the third dosage strength is greater than the second dosage strength; the third dosage form has a steady state $C_{ave}$, a steady state AUC and a single dose $C_{max}$; the steady state $C_{ave}$ and the steady state AUC of the first dosage form, the second dosage form and the third dosage form are each dose proportional with respect to each other; and the single dose $C_{max}$ of the third dosage form is less than the minimum level for dose proportionality with respect to the second dosage form, wherein the third dosage form is a sustained release dosage form; and wherein the third dosage form is a tablet, a capsule, a caplet or a gelcap; and wherein the third dosage form does not comprise a portion of the opioid in immediate release form.

9. The kit of claim 8 wherein the single dose $C_{max}$ of the third dosage form is 75% or less of the single dose $C_{max}$ of the second dosage form times the dosage strength ratio of the third dosage form to the second dosage form.

10. The kit of claim 8 wherein the first dosage form, the second dosage form and the third dosage form each have a single dose AUC and the single dose AUC of the first dosage form, the second dosage form and the third dosage form are each dose proportional.

11. The kit of claim 8, wherein the opioid is hydrocodone.

12. The kit of claim 1, further comprising a set of printed instructions directing the administration of the first dosage form to the patient, and thereafter, the administration of the second dosage form to the patient.

13. The kit of claim 1, wherein the first dosage form comprises a first multiparticulate system, and wherein the second dosage form comprises a second multiparticulate system.

14. The kit of claim 13, wherein the first multiparticulate system and the second multiparticulate system each comprises a plurality of granules, spheroids, or pellets.

15. A kit comprising: a) a first dosage form comprising a first dosage strength of hydrocodone; and b) a second dosage form comprising a second dosage strength of hydrocodone; wherein the second dosage strength is greater than the first dosage strength; wherein the first dosage form and the second dosage form each have a steady state $C_{ave}$, a steady state AUC and a single dose $C_{max}$; wherein the steady state $C_{ave}$ and the steady state AUC of the first dosage form and the second dosage form are dose proportional and the single dose $C_{max}$ of the second dosage form is less than the minimum level for dose proportionality with respect to the first dosage form; wherein the first dosage form and the second dosage form are each sustained release dosage forms; wherein the first dosage form and the second dosage form are each a tablet, a capsule, a caplet or a gelcap; and wherein the first dosage form and the second dosage form do not comprise a portion of the hydrocodone in immediate release form.

16. The kit of claim 15, wherein the first dosage form and the second dosage form each have a single dose AUC and the single dose AUC of the first dosage form and the second dosage form are dose proportional.

17. The kit of claim 16, wherein the first dosage form and the second dosage form are each oral dosage forms.

18. The kit of claim 15, wherein the first dosage form and the second dosage form are each oral dosage forms.

19. The kit of claim 15 wherein single dose $C_{max}$ of the second dosage form is 75% or less of the $C_{max}$ of the first dosage form times the dosage strength ratio of the second dosage form to the first dosage form.

20. The kit of claim 15, wherein the single dose $C_{max}$ of the second dosage form is 70% or less of the $C_{max}$ of the first dosage form times the dosage strength ratio of the second dosage form to the first dosage form.

21. The kit of claim 15, wherein the single dose $C_{max}$ of the second dosage form is 65% or less of the $C_{max}$ of the first dosage form times the dosage strength ratio of the second dosage form to the first dosage form.

22. The kit of claim 15, wherein the $C_{max}$ of the second dosage form is 60% or less of the $C_{max}$ of the first dosage form times the dosage strength ratio of the second dosage form to the first dosage form.

23. The kit of claim 15, wherein the first dosage form comprises a first multiparticulate system, and wherein the second dosage form comprises a second multiparticulate system.

24. The kit of claim 23, wherein the first multiparticulate system and the second multiparticulate system each comprises a plurality of granules, spheroids, or pellets.

* * * * *